United States Patent
Zaninovic et al.

(10) Patent No.: US 12,014,833 B2
(45) Date of Patent: Jun. 18, 2024

(54) SYSTEM AND METHOD FOR SELECTING ARTIFICIALLY FERTILIZED EMBRYOS

(71) Applicants: Cornell University, Ithaca, NY (US); Yale University, New Haven, CT (US)

(72) Inventors: Nikica Zaninovic, New York, NY (US); Olivier Elemento, New York, NY (US); Iman Hajirasouliha, New York, NY (US); Pegah Khosravi, New York, NY (US); Jonas Malmsten, Gibsonton, FL (US); Zev Rosenwaks, New York, NY (US); Qiansheng Zhan, New York, NY (US); Ehsan Kazemi, New Haven, CT (US)

(73) Assignees: Cornell University, Ithaca, NY (US); Yale University, New Haven, CT (US)

( * ) Notice: Subject to any disclaimer, the term of this patent is extended or adjusted under 35 U.S.C. 154(b) by 516 days.

(21) Appl. No.: 17/266,300

(22) PCT Filed: Aug. 6, 2019

(86) PCT No.: PCT/US2019/045283
§ 371 (c)(1),
(2) Date: Feb. 5, 2021

(87) PCT Pub. No.: WO2020/033391
PCT Pub. Date: Feb. 13, 2020

(65) Prior Publication Data
US 2021/0272282 A1    Sep. 2, 2021

Related U.S. Application Data

(60) Provisional application No. 62/715,518, filed on Aug. 7, 2018.

(51) Int. Cl.
*G06T 7/00* (2017.01)
*G06N 3/08* (2023.01)
(Continued)

(52) U.S. Cl.
CPC ........... *G16H 50/30* (2018.01); *G06N 3/08* (2013.01); *G06T 7/0012* (2013.01);
(Continued)

(58) Field of Classification Search
CPC ........ G16H 50/20; G16H 30/20; G16H 30/40; G16H 50/30; G16H 70/60; G16H 10/60;
(Continued)

(56) References Cited

U.S. PATENT DOCUMENTS 10,607,338 B2 * 3/2020 Ngadi .................. G06F 18/24
11,670,417 B2 * 6/2023 Banerjee ............ G06V 10/7715
702/19

(Continued)

FOREIGN PATENT DOCUMENTS

WO    2019068073 A1    4/2019
WO    2019113643 A1    6/2019

OTHER PUBLICATIONS

International Search Report and Written Opinion dated Nov. 20, 2019 in International Application No. PCT/US2019/045283.
(Continued)

*Primary Examiner* — Congvan Tran
(74) *Attorney, Agent, or Firm* — McDermott Will & Emery LLP

(57) ABSTRACT

A method for classifying human blastocysts includes obtaining images of a set of artificially fertilized (AF) embryos incubating in an incubator. A morphological quality of the AF embryos is determined based on a classification of the images by a convolutional neural network trained using images of pre-classified embryos. Each of the AF embryos is graded based on the morphological quality. A probability that a given graded AF embryo will result in a successful pregnancy after the given AF embryo is implanted in a gestating female is computed for each of the AF embryos (Continued)

from the set based on a grade of the given AF embryo and clinical parameters associated with the gestating female. One or more graded AF embryos to be recommended to be implanted in the gestating female from the set are selected based on the probability of successful pregnancy. An identity of each of the selected graded AF embryos and a number of the selected graded AF embryos to be potentially implanted in the gestating female is then output based on an outcome desired by the gestating female following implantation.

19 Claims, 5 Drawing Sheets

(51) Int. Cl.
| | |
|---|---|
| *G06V 10/44* | (2022.01) |
| *G06V 10/82* | (2022.01) |
| *G06V 20/69* | (2022.01) |
| *G16H 10/60* | (2018.01) |
| *G16H 30/20* | (2018.01) |
| *G16H 50/20* | (2018.01) |
| *G16H 50/30* | (2018.01) |
| *G16H 50/70* | (2018.01) |
| *G16H 70/60* | (2018.01) |

(52) U.S. Cl.
CPC ............ *G06V 10/454* (2022.01); *G06V 10/82* (2022.01); *G06V 20/69* (2022.01); *G06V 20/698* (2022.01); *G16H 10/60* (2018.01); *G16H 30/20* (2018.01); *G16H 50/20* (2018.01); *G16H 50/70* (2018.01); *G16H 70/60* (2018.01); *G06T 2207/20036* (2013.01); *G06T 2207/20081* (2013.01); *G06T 2207/20084* (2013.01); *G06T 2207/30044* (2013.01)

(58) Field of Classification Search
CPC .................. G16H 50/70; G06T 7/0012; G06T 2207/30044; G06T 2207/20081; G06T 2207/20036; G06T 2207/20084; G06V 10/454; G06V 20/698; G06V 20/69; G06V 10/82; G06N 3/08
See application file for complete search history.

(56) References Cited

U.S. PATENT DOCUMENTS

| | | | |
|---|---|---|---|
| 2013/0165744 A1* | 6/2013 | Carson | ................. A61K 31/575 600/34 |
| 2014/0247972 A1* | 9/2014 | Wang | .................... G06F 18/214 382/133 |
| 2014/0249363 A1* | 9/2014 | Yamashita | ......... G01N 33/9433 600/34 |
| 2017/0283754 A1* | 10/2017 | Petersen | ............ G02B 21/0084 |
| 2019/0042958 A1* | 2/2019 | Letterie | ................ G06V 20/698 |
| 2021/0287373 A1* | 9/2021 | Murata | .............. H04N 1/00167 |

OTHER PUBLICATIONS

Patil, Sujata N., et al. "Deep learning techniques for automatic classification and analysis of human in vitro fertilized (IVF) embryos" Journal of Emerging Technologies and Innovative Research, vol. 5, Issue 2, pp. 100-106, Feb. 28, 2018.

Kheradmand, Shakiba. "Human Embryo Component Detection using Computer Vision" PhD diss., Applied Sciences: School of Engineering Science, 2017.

Khosravi, Pegah, et al. "Deep Neural Networks Reliably Assess Human Blastocyst Quality and Assist in Predicting Implantation Success upon In Vitro Fertilization" NPJ Digital Medicine, vol. 2, No. 1, Apr. 4, 2019.

Examination Report issued in corresponding European Patent Application No. 19759122.5 dated Feb. 9, 2023 (6 pages).

Official Action issued in corresponding Israeli Patent Application No. 280645 dated Jul. 5, 2023 (3 pages).

\* cited by examiner

SYSTEM AND METHOD FOR SELECTING ARTIFICIALLY FERTILIZED EMBRYOS

CROSS REFERENCE TO RELATED APPLICATIONS

This application is a United States National Phase under 35 U.S.C. § 371 of International Application No. PCT/US2019/045283 filed on Aug. 6, 2019, which claims the benefit of, and priority to, U.S. Provisional Patent Application No. 62/715,518, entitled "SYSTEM AND METHOD FOR SELECTING ARTIFICIALLY FERTILIZED EMBRYOS" filed on Aug. 7, 2018, both of which are hereby incorporated by reference in their entirety for all purposes.

BACKGROUND

Assessing quality of embryos and selecting human blastocysts for transfer in in vitro fertilization (IVF) is challenging because it remains highly subjective and prone to biases in human judgement and differences in perception among embryologists. More objective measures are needed to reliably predict quality of embryos without human intervention.

SUMMARY

In an aspect of the present disclosure, a method for classifying human blastocysts includes obtaining images of a set of artificially fertilized (AF) embryos incubating in an incubator. A morphological quality of the AF embryos is determined based on a classification of the images by a convolutional neural network. The convolutional neural network is trained using images of pre-classified embryos and grading each of the AF embryos based on the morphological quality. A probability that a given graded AF embryo will result in a successful pregnancy after the given AF embryo is implanted in a gestating female for each of the AF embryos from the set is calculated based on a grade of the given AF embryo and clinical parameters associated with the gestating female. Graded AF embryos to be recommended to be implanted in the gestating female are selected from the set based on the probability of successful pregnancy and an outcome desired by the gestating female following implantation. An identity and number of the selected AF embryos is then outputted.

In some implementations, the images are obtained at one or more predetermined points in time after fertilization. In some implementations, the images include images of multiple planes of the AF embryos.

In some implementations, the selected AF embryos provide the highest likelihood of live birth following implantation of the selected AF embryos in the gestating female.

In some implementations, the morphological quality of the AF embryos is classified as good, fair and poor.

In some implementations, the images of pre-classified embryos used for training the convolutional neural network include images of pre-classified embryos taken at two different times post-fertilization and at seven different planes across each of the pre-classified embryo. In some implementations, the images of pre-classified embryos are classified as good, fair and poor.

In some implementations, the images of the set of AF embryos are unprocessed bright field images using a Hoffman modulation contrast objective.

In some implementations, the convolutional neural network is trained using the pre-classified embryos and clinical data associated with the pre-classified embryos, the clinical data associated with the pre-classified embryos comprising age of a donor female providing eggs that were fertilized to obtain the pre-classified embryos and presence of clinical conditions associated with the donor female, the clinical conditions including diabetes and obesity.

In some implementations, the clinical parameters associated with the gestating female include age of the gestating female and presence of clinical conditions associated with the gestating female, the clinical conditions including diabetes and obesity.

In another aspect of the present disclosure, a system for classifying human blastocysts includes an input module, a morphological quality evaluation module, a pregnancy success computing module, and an embryo selection module. The input module is configured to receive images of a set of artificially fertilized (AF) embryos incubating in an incubator. The morphological quality evaluation module is configured to determine a morphological quality of the AF embryos based on a classification of the images by a deep neural network trained using images of pre-classified embryos. The pregnancy success computing module is configured to compute a probability that a given AF embryo will result in a successful pregnancy after the given AF embryo is implanted in a gestating female for each of the AF embryos from the set based on the morphological quality of the AF embryos and clinical parameters associated with the gestating female. The embryo selection module is configured to select one or more of the AF embryos from the set based on the probability of successful pregnancy, and to output an identity of each of the selected graded AF embryos and a number of the selected graded AF embryos to be recommended to be implanted in the gestating female based on a desired outcome input into the embryo selection module following implantation.

In some implementations, the deep neural network is a convolutional neural network and the images of pre-classified embryos are unprocessed bright field micrographs of the pre-classified embryos. In some implementations, the images of AF embryos and the pre-classified images are monochrome images.

In some implementations, the embryo selection module is configured select AF embryos that provide a highest likelihood of live birth following implantation of the AF embryos in the gestating female.

In some implementations, the number of the selected AF embryos to be implanted into the gestating female is determined based on an aggregate probability that the number and identity of selected AF embryos will result in a highest likelihood of live birth following implantation of the AF embryos in the gestating female.

In some implementations, the clinical parameters associated with the gestating female include age of the female and presence of clinical conditions including diabetes and obesity.

In yet another aspect of the present disclosure, a non-transitory computer readable medium storing a computer readable program of classifying human blastocysts, includes computer readable instructions to determine a morphological quality of artificially fertilized (AF) embryos based on a classification of images of the AF embryos by a convolutional neural network trained using images of pre-classified embryos. Computer readable instructions to compute a probability that a given AF embryo will result in a successful pregnancy after the given AF embryo is implanted in a gestating female for each of the AF embryos from the set are further included. The probability is computed based on the morphological quality of the given AF embryo and clinical parameters associated with the gestating female. Additionally, computer readable instructions to select one or more of the AF embryos from the set based on the morphological quality of the AF embryos and clinical parameters associated with the gestating female, and provide an identity and number of AF embryos from the set that will provide the highest likelihood of live birth following implantation in the gestating female are included.

In some implementations, the clinical parameters associated with the gestating female include age and presence of clinical conditions including diabetes and obesity.

In some implementations, the number of the selected AF embryos to be implanted into the gestating female is determined based on an aggregate probability that the number and identity of selected AF embryos will result in a highest likelihood of live birth following implantation of the AF embryos in the gestating female.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
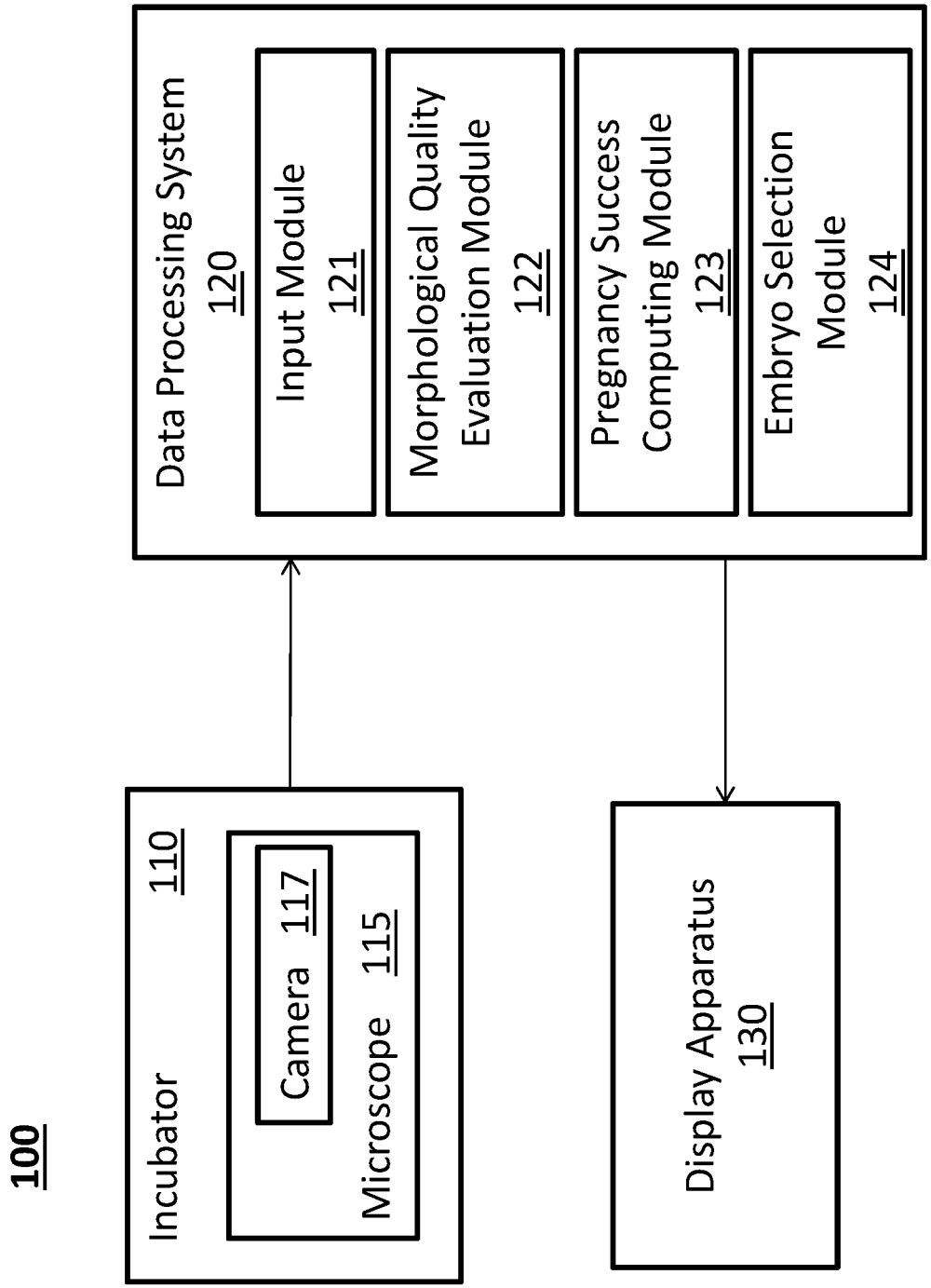
FIG. 1 schematically illustrates a system for classifying human blastocysts in accordance with an implementation of the present disclosure.

The various concepts introduced above and discussed in greater detail below may be implemented in various ways, as the described concepts are not limited to any particular manner of implementation. Examples of specific implementations are provided for illustrative purposes.

Infertility affects about 186 million people worldwide. In the United States, infertility affects approximately 8% of women of child-bearing age. Approximately 44% of women in the U.S. meet criteria for infertility at a certain point during their reproductive years. Assisted reproductive technology (ART), including in vitro fertilization (IVF), is one of the most common treatments for infertility. IVF involves ovarian stimulation followed by the retrieval of multiple oocytes from the growing follicles, fertilization, and embryo culture for 1-6 days in controlled environmental conditions. Embryo quality is then assessed to select one or more embryos for transfer to the patient's uterus. One reason that multiple embryos are transferred is the absence of a highly accurate and reliable method for selecting good-quality embryos. Although IVF and embryo-transfer technologies have improved considerably over the past 30 years, their efficacy remains relatively low.

Conventional embryo evaluation involves observation, assessment, and manual grading of the morphological features of blastocysts by skilled embryologists. While this method is used widely in the clinical practice for selection and transfer, evaluating a single static image and basing decisions on a rough estimation of embryos is subjective and can be time-consuming.

There is also inconsistency in blastocyst classification and associated grading systems among medical centers, which has made it very challenging to compare methods and analyze patients who have undergone treatments in different clinics. To date, attempts to establish a universal grading and selection system have failed.

Improving the ability to determine which embryos have the highest implantation potential would help increase pregnancy success rates. It would also minimize the chance of multiple births due to the transfer of more embryos that may be needed to achieve a live birth as a way to increase the success rate. Opportunities exist to leverage artificial intelligence (AI), as IVF clinics have long adopted digital imaging as part of their clinical practice and have accumulated thousands of labeled images and time-lapse datasets. Time-lapse imaging (TLI) is an emerging technology that allows continuous observation of embryo development without removing embryos from controlled and stable incubator conditions. Time-lapse analysis was first used more than three decades ago to study the development of bovine embryos in vitro. Interest in using this technology to assess clinical embryos has recently grown, as it has been shown to improve selection of the most robust embryos for transfer. This technology also improved IVF cycle outcomes by decreasing the embryos' exposure to changes in temperature, high oxygen, and fluctuations in pH during culture. In addition, it has enabled embryologists to assess embryo quality by tracking the timing of embryo cleavage events and the length of different intervals of embryo development (karyokinesis and cytokinesis).

Currently, no robust and fully automatic method exists to analyze human embryo data from TLI. A few groups have attempted to use different machine learning approaches for embryo quality analysis, with varying degrees of success for bovine and mammalian oocytes using artificial neural network (ANN)- and random forest (RF)-based classification, respectively. Their results showed 76.4% (test set=73 embryos) and 75% (test set=56 embryos) accuracy for discretization of bovine embryo grades (excellent, fair, and poor) and mammalian oocyte grades (A, B, C, and D), respectively. Furthermore, a few previously published approaches have focused on classifying human embryo quality based on specific features, such as the inner cell mass (ICM) area, trophectoderm (TE) area, and zona pellucida (ZP) thickness, and the blastocyst area and radius separately. In particular, a study by Filho et. al. (Hum. Reproduction 27, 2641-2648 (2012)) presented a semi-automatic grading of human embryos. They showed that classifiers can have different accuracies for each object (blastocyst extension, ICM, and TE). Their results indicated various accuracy ranges from 67% to 92% for the embryo extension, from 67% to 82% for the ICM, and from 53% to 92% for the TE detection; 92% was the highest accuracy achieved across the 73-embryo test set. Although these methods achieved a reasonable accuracy in assessing human embryo quality, they require advanced embryology expertise and several preprocessing steps, which is time-consuming.

FIG. 1 illustrates a system for classifying human blastocysts. The system 100 includes an incubator 110, a data processing system 120 and a display apparatus 130.

The incubator 110, in some implementations, includes an apparatus in which human embryos are be incubated. In some implementations, the incubator 110 maintains an environment within the incubator where the partial pressure of oxygen is reduced to about 5% (compared to about 20% in the atmosphere). The incubator 110 may, in some implementations, use an artificial culture medium or an autologous endometrial coculture for culturing the embryos. In some implementations, the incubator 110 allows change of culture medium after a certain period of time. For example, the embryos may be cultured in a first medium for 3 days and then the culture medium is changed to a second medium thereafter.

In an implementation, the incubator 110 further includes a built-in microscope 115 for imaging the embryos. In an implementation, the microscope 115 uses a Hoffman modulation contrast objective, and images the embryos at, for example, a magnification of about 20×. In some embodiments, the microscope 115 uses a single wavelength light having a wavelength, for example, of 635 nm.

The microscope 115, in some implementations, includes a camera 117 which is configured to capture images of the embryos as desired or at predetermined time periods. In some implementations, the camera 117 has a resolution of about 1280×1024 pixels, and images an area of the embryos such as to provide 3 pixels/µm. In an implementation, the camera captures 8-bit monochrome images. In an implementation, the embryos are illuminated for a period about 0.032s for capture of an image. In some implementations, the camera 117 is configured to capture an image of the embryo at predetermined periods of time. For example, the camera 117 may capture images every 5 minutes, every 10 minutes, every 15 minutes, every hour, and so forth. Additionally, the camera 117 may capture an image of several planes of the embryo every time an image is captured. For example, every time an image is to be captured, the microscope 115 may focus on several different planes, e.g., 3, 5, 7 or more planes, and the camera 117 captures an image at each of the several different planes. Thus, in some implementations, microscope 115 captures 7 images every 15 minutes. In other implementations, the microscope 115 captures 5 images every 20 minutes, and so forth.

Referring back to FIG. 1, the system 100 includes a data processing system 120. As can be seen in FIG. 1, the data processing system 120 further includes an input module 121, a morphological quality evaluation module 122, a pregnancy success computing module 123, and an embryo selection module 124.

The input module 121 receives images from the microscope 115 for further processing. In an implementation, the input module 121 includes a computer-readable non-volatile storage configured to store images such as, for example, a hard disk drive, integrated circuit memory (e.g., a flash memory), a tape drive, or access to a shared memory storage such as a cloud storage drive. In an implementation, the input module 121 is configured to store the images in an uncompressed form as received from the microscope 115. In some implementations, the input module 121 is configured to standardize the images received from the microscope 115. For example, the images received from the microscope 115 are processed to select an area that includes at least one whole embryo. In an implementation, the input module 121 may also be configured to normalize the brightness of the images received from the microscope 115.

The input module 121 may also be configured to receive a request to select a particular set of images, and upon receiving such request, select the requested images and provide them to the morphological quality evaluation module 122 (or any the module of the system 100) for further processing. For example, the input module 121 may be requested to provide images of embryos acquired at 110 hours post-insemination for a particular subject. Upon receiving such a request, the input module 121 may retrieve all of the images (e.g., images of 7 planes of all of the embryos) for the subject at 110 hours post-insemination, and provide those images to, for example, the morphological quality evaluation module 122 for further processing. In some implementations, images acquired at other or additional time points may be requested for use in further analysis. For example, in an implementation, images acquired at 66 hours and 110 hours may be requested. In other implementations, images acquired at 66 hours, 110 hours and 120 hours may be requested.

The morphological quality evaluation module 122 is configured to determine a morphological quality of the embryos by analyzing the images received from the input module 121. The morphological quality evaluation module 122 may further include one or more processors for running a deep neural network (DNN) algorithm. The one or more processors may be local, forming a server or a cluster, or distributed in the cloud. In an implementation, the DNN includes a convolutional neural network (CNN). For example, in an implementation, the DNN is based on Inception-V1 architecture by Google, Inc.

Figure 2:
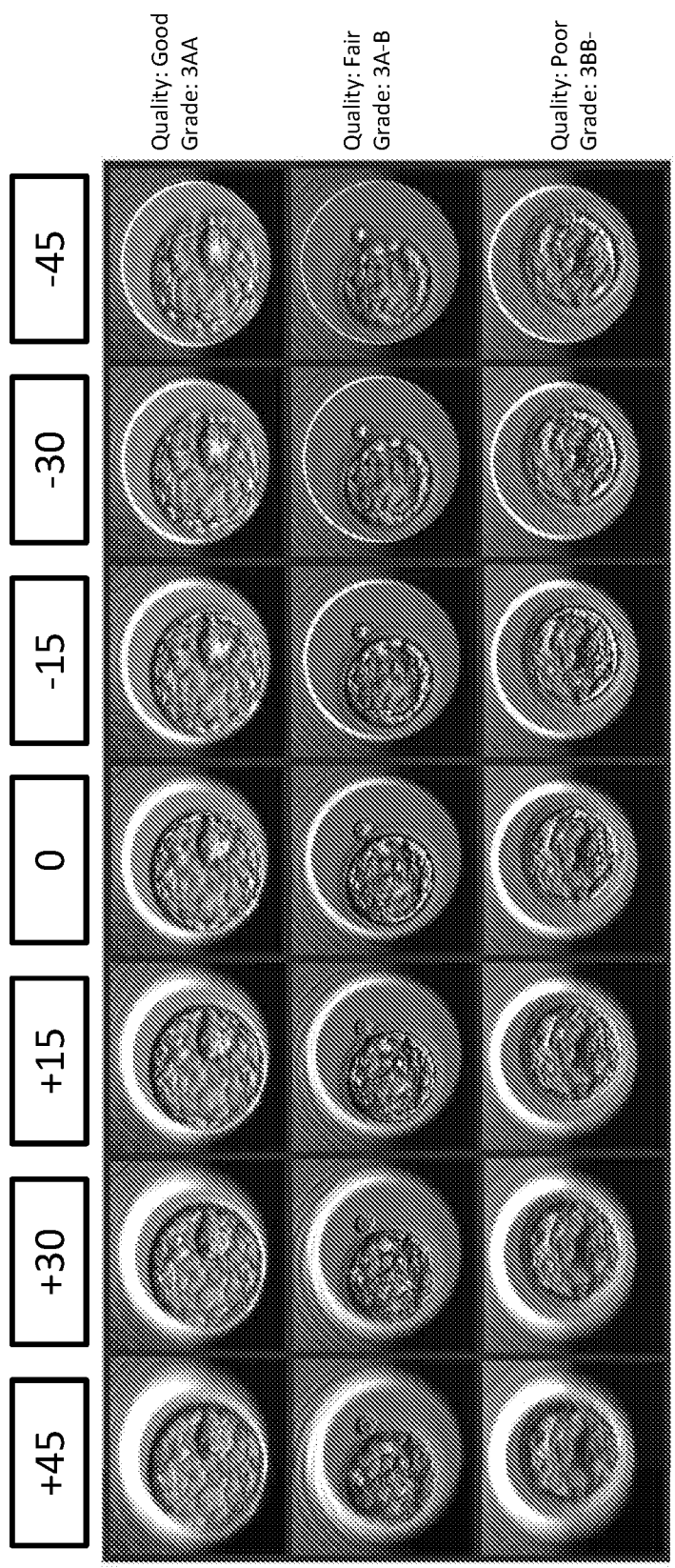
FIG. 2 shows embryo images across seven focal planes classified as good, fair and poor based on a Veeck and Zaninovic grade.

The DNN, in an implementation, is trained to classify embryos as good, fair or poor based on an analysis of images received from the input module 121. In some implementations, the DNN is trained using raw images of embryos that are pre-classified. The pre-classification may include grading an embryo based on values for each of a set of parameters (such as, for example, blastocyst expansion, cell abundance, conformity in inner cell mass (ICM), trophectoderm (TE) and/or zona pellucida (ZP)) into a composite grade. The composite grade may use one or more of clinically accepted systems of grading such as, for example, the Veeck and Zaninovic grading system, the Gardner grading system or the Asebir grading system. In an implementation, grading the embryo further involves classifying the composite grade into good, fair or poor. In an implementation, the composite grade is classified into good and poor. An example of how the composite grades (using the Veeck and Zaninovic grading system) are classified into good and poor is provided in Table 1. An example of how the embryo images are classified into good, fair and poor based on a Veeck and Zaninovic grade is shown in FIG. 2.

TABLE 1

Classification of composite grades (using the Veeck and Zaninovic grading system) into good and poor.

| The list of grades | The quality map |
| --- | --- |
| 3-4AA, 4A-A, 4A-A-, 5AA-, 4AB, 5A-A-, 4AA-, 4AA, 3A-A, 3AA, 3AA-, 3AB, 3A-A- | good-quality |
| 1-2B-/CB, 1-2B-/CB-/C, 1-2B-C, 1B-/CB-/C, 1BC, 1CB-/C, 1CC, 2-2B-C, 2-3BC, 3B-B-/B, 3BC, 3CA-3CB, 3CB-, 3CC, 1-2B-/CB-, 1B-/CB, 1B-/CB-, 1B-/CC, 2-3B-/CB, 2-3B-/CB-, 2B-/CB, | poor-quality |

TABLE 1-continued

Classification of composite grades (using the Veeck and Zaninovic grading system) into good and poor.

| The list of grades | The quality map |
|---|---|
| 3B-/CB-/C, 3B-/CC, 1-2BB-/C, 2B-/CB-/C, 3B-C, 1BB-/C, 1BB-/C, 1-2B-B-/C, 1B-C, 2-3BB-/C, 2-3B-B-/C, 2B-/CB-, 3B-/CB-, 3B-/CB, 2BB-/C, 1B-B-/C, 2B-B-/C, 3BB-/C, 3B-B-/C, 1-2B-B, 1-2B-B-, 2-3B-B-, 1-2BB-, 2-3B-B, 1B-B, 1BB-, 2-3BB-, 1-2BB, 1B-B-, 2B-B, 2B-B-, 2BB-, 3B-B-, 1BB, 2BB, 3B-B, 3BB- | |

In some implementations, the training of the DNN is fine-tuned by analyzing the embryo images using the trained DNN, and if necessary reclassifying the images as good, fair or poor (or, e.g., good or poor; or excellent, good, average, acceptable or poor, or other classification schemes with at least two classes) using either classification by a human expert or by using clinical outcome data. For example, in an implementation, training the DNN further involves providing the DNN with clinical data associated with the pre-classified embryos. For example, clinical data associated with the donor female whose egg is fertilized to form the embryo is input in the DNN. The clinical data may include, without limitation, age of the donor female, incidence of clinical conditions such as diabetes, obesity, etc. in the donor female, genetic history (e.g., incidence of Down's syndrome in the family) of donor female, etc. In some implementations, training the DNN further includes feeding back the clinical outcomes of implantation of graded embryos. For example, for each of the embryos classified as good, fair or poor, the incidence of successful (or unsuccessful) pregnancy following implantation of the embryo(s) into a gestating female is fed back into the DNN.

Referring back to FIG. 1, the data processing system 120 further includes a pregnancy success computing module 123. In an implementation, the pregnancy success computing module 123 is configured to compute a probability that a given embryo will result in a successful pregnancy after the given embryo is implanted in a gestating female. In an implementation, the probability of successful pregnancy is computed based on, for example, a grade of the embryo provided by the morphological quality module and clinical parameters associated with the gestating female. The clinical parameters may include, without limitation, age of the gestating mother, incidence of clinical conditions such as diabetes, obesity, etc. in the gestating female, genetic history of the gestating female, etc. It must be noted that the donor female and the gestating female may be same or different individual.

Figure 3:
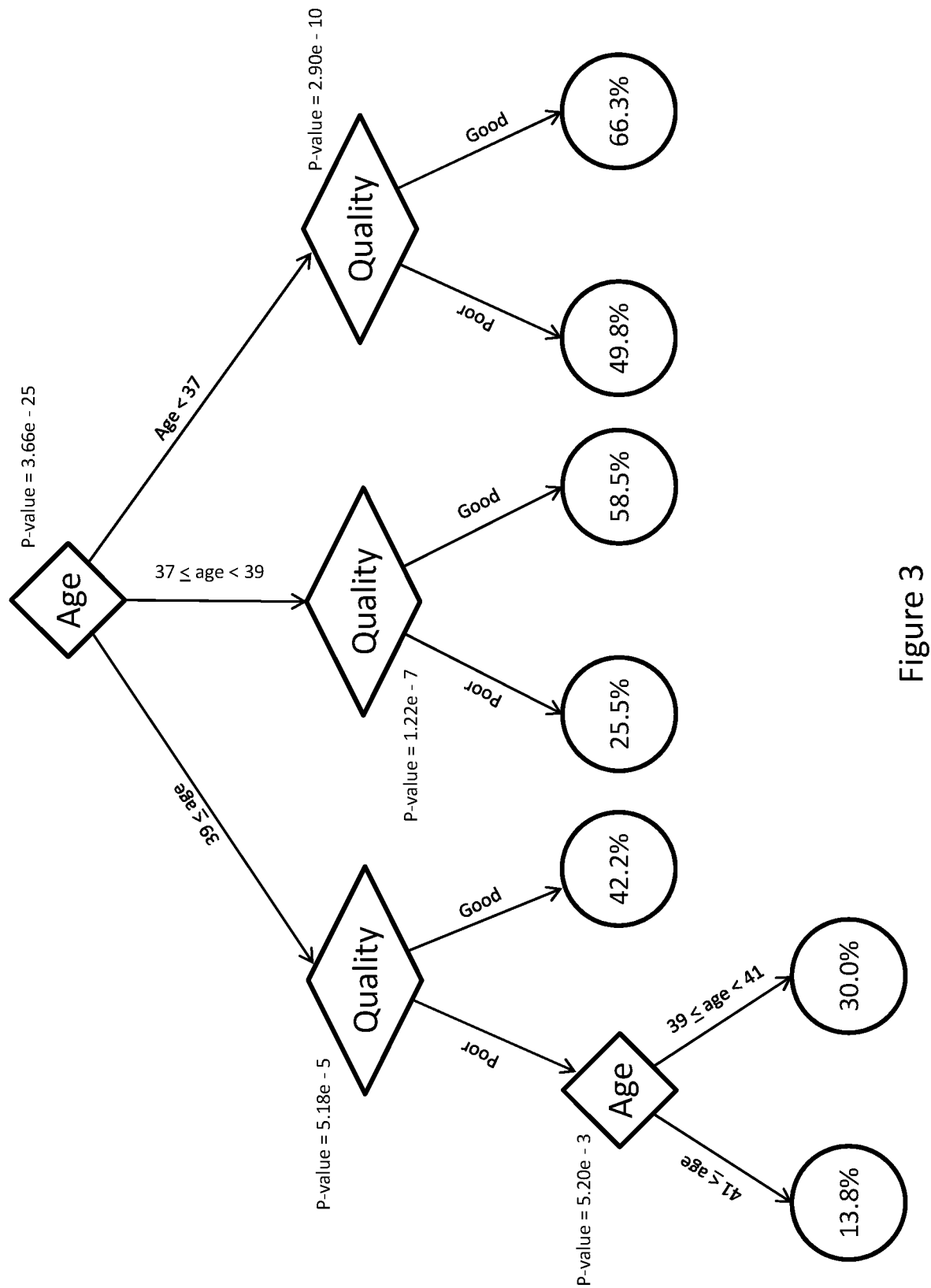
FIG. 3 schematically illustrates a decision tree based on the CHAID algorithm, showing interaction between age of the gestating female and embryo quality.

In an implementation, as illustrated in FIG. 3, the probability of successful pregnancy is computed using a hierarchical type class decision tree such as, for example, a chi-squared automatic interaction detection (CHAID) algorithm. In an implementation, the CHAID algorithm uses a grade of the embryo (e.g., good or bad, based on its morphological quality) and age of the gestating female to compute the probability of successful pregnancy. In an implementation of the CHAID algorithm, optimal multi-way splits are identified using chi-squared statistics. The algorithm further includes identification of a set of characteristics (e.g., embryo grade and gestating female's age in the example of FIG. 3) that best differentiate individuals (i.e., gestating females) based on a categorical outcome (e.g., successful pregnancy or live birth, premature birth, full term pregnancy, unsuccessful pregnancy, etc.) to create exhaustive and mutually exclusive subgroups of individuals. Best partitions (e.g., partitions of age and embryo grade in the example of FIG. 3) are then chosen based on the basis of statistical significance. In an implementation, Bonferroni-adjusted p-values are used to determine significance with a predetermined minimum size of end nodes.

As shown in FIG. 3, for example, the CHAID algorithm may result in a decision tree in which gestating females are classified into three age groups: (i) age less than 36 years, (ii) age 37 and 38 years, and (iii) age greater than 39 years (e.g., with sub-groups of 39 years to 41 years, and greater than 41 years for poor quality embryos). For each age group, embryos may be discretized in good-quality and poor-quality groups. As shown, with this decision tree, a probability of successful pregnancy for a particular gestating female of a particular age can be computed for each embryo (e.g., by identifying a probability "box" for that embryo and gestating female, such as the 13.8% box, the 30.0% box, the 42.2% box, the 25.5% box, the 58.5% box, the 49.8% box, or the 66.3% box as shown, based on the embryo grade and the age).

Referring back to FIG. 1, the data processing system 120 further includes an embryo selection module 124. The embryo selection module is configured to select one or more of the embryos (whose morphological quality has been graded by the morphological quality evaluation module 122) based on the probability of successful pregnancy determined by the pregnancy success computing module 123. The selected embryos are then identified based on the probability of successful pregnancy associated with each of them, and the identity and number of selected embryos to be implanted in the gestating female is output based on a desired outcome following implantation. For example, a 32 year old gestating female may desire only one live birth as an outcome following implantation. In such as case, if there are 5 graded embryos with a probability of successful pregnancy of P1, P2, P3, P4 and P5 respectively based on the morphological quality and her age of 32 years, the embryo selection module 124 may select the embryos with probabilities of P1 and P4 to implant in the gestating female so as to increase the likelihood of pregnancy that will result in only one live birth. On the other hand, a 39 year old gestating female may desire at least one live birth, notwithstanding the potential for multiple live births, as an outcome following implantation. In such case, if there are 5 graded embryos with a probability of successful pregnancy of P1', P2', P3', P4' and P5' respectively based on the morphological quality and her age of 39 years, the embryo selection module 124 may select the embryos with probabilities of P2', P3' and P5' to implant in the gestating female so as to increase the likelihood of pregnancy that will result in at least one live birth, notwithstanding the probability of multiple live births.

The embryo selection module 124 outputs the identity and number of selected embryos to display 130 which displays the identity and number of the selected embryos to the clinician. The clinician may then use his/her expertize and/or exercise his/her judgement in consultation with the gestating female (and/or her family) to act on the recommendation output by the system 100 about the number and identity of embryos to potentially implant.

Figure 4:
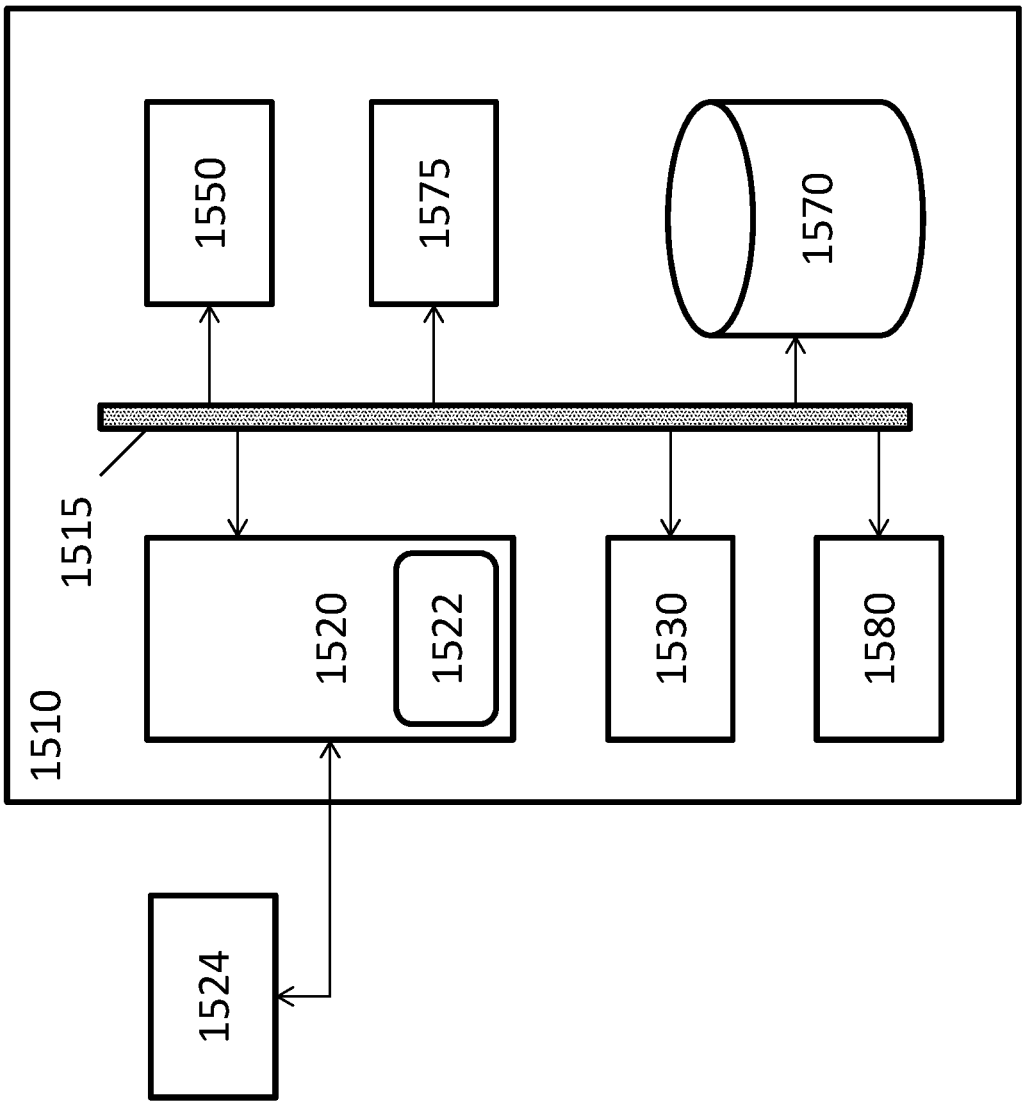
FIG. 4 schematically illustrates a block diagram of an example computing system.

FIG. 4 illustrates a block diagram of an example computing system 1500. In some implementations, the computing system 1500 may be utilized in implementing the data processing system 120, and/or any of the processors or modules within the data processing system 120 illustrated in FIG. 1.

In broad overview, the computing system 1510 includes at least one processor 1550 for performing actions in accordance with instructions and one or more memory devices 1570 or 1575 for storing instructions and data. The illustrated example computing system 1510 includes one or more processors 1550 in communication, via a bus 1515, with at least one network interface controller 1520 with network interface ports 1522(*a-n*) connecting to other computing devices 1524(*a-n*), memory 1570, and any other devices 1580, e.g., an I/O interface. Generally, a processor 1550 will execute instructions received from memory. The processor 1550 illustrated incorporates, or is directly connected to, cache memory 1575.

In more detail, the processor 1550 may be any logic circuitry that processes instructions, e.g., instructions fetched from the memory 1570 or cache 1575. In many embodiments, the processor 1550 is a microprocessor system or special purpose processor. The computing device 1500 may be based on any processor, or set of processors, capable of operating as described herein. In some implementations, the processor 1550 can be capable of implementing and/or executing any of the input module 121, the morphological quality evaluation module 122, the pregnancy success computing module 123 and/or the embryo selection module 124. The processor 1550 may be a single core or multi-core processor. The processor 1550 may be multiple processors. In some implementations, the processor 1550 can be configured to run multi-threaded operations. In some implementations, the processor 1550 may host one or more virtual machines or containers, along with a hypervisor or container manager for managing the operation of the virtual machines or containers.

The memory 1570 may be any device suitable for storing computer readable data. The memory 1570 may be a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, and BluRay® discs). A computing system 1500 may have any number of memory devices 1570. In some implementations, the memory 1570 can include instructions corresponding to the human blastocyst classification system described with reference to FIG. 1. In some implementations, the memory 1570 supports virtualized or containerized memory accessible by virtual machine or container execution environments provided by the computing system 1510.

The cache memory 1575 is generally a form of computer memory placed in close proximity to the processor 1550 for fast read times. In some implementations, the cache memory 1575 is part of, or on the same chip as, the processor 1550. In some implementations, there are multiple levels of cache 1575, e.g., L2 and L3 cache layers.

The network interface controller 1520 manages data exchanges via the network interfaces 1522(*a-n*) (also referred to as network interface ports). The network interface controller 1520 handles the physical and data link layers of the OSI model for network communication. In some implementations, some of the network interface controller's tasks are handled by the processor 1550. In some implementations, the network interface controller 1520 is part of the processor 1550. In some implementations, a computing system 1510 has multiple network interface controllers 1520. The network interfaces 1522(*a-n*) are connection points for physical network links. In some implementations, the network interface controller 1520 supports wireless network connections and an interface port 1522 is a wireless receiver/transmitter. Generally, a computing device 1510 exchanges data with other computing devices 1512(*a-n*) via physical or wireless links to a network interfaces 1522(*a-n*). In some implementations, the network interface controller 1520 implements a network protocol such as Ethernet.

The other computing devices 1524(*a-n*) are connected to the computing device 1510 via a network interface port 1522. The other computing devices 1524(*a-n*) may be peer computing devices, network devices, or any other computing device with network functionality. For example, a first computing device 1524(*a*) may be a network device such as a hub, a bridge, a switch, or a router, connecting the computing device 1510 to a data network such as the Internet.

The other devices 1580 may include an I/O interface, external serial device ports, and any additional co-processors. For example, a computing system 1510 may include an interface (e.g., a universal serial bus (USB) interface) for connecting input devices (e.g., a keyboard, microphone, mouse, or other pointing device), output devices (e.g., video display, speaker, or printer), or additional memory devices (e.g., portable flash drive or external media drive). In some implementations, a computing device 1500 includes an additional device 1580 such as a coprocessor, e.g., a math co-processor can assist the processor 1550 with high precision or complex calculations.

Figure 5:
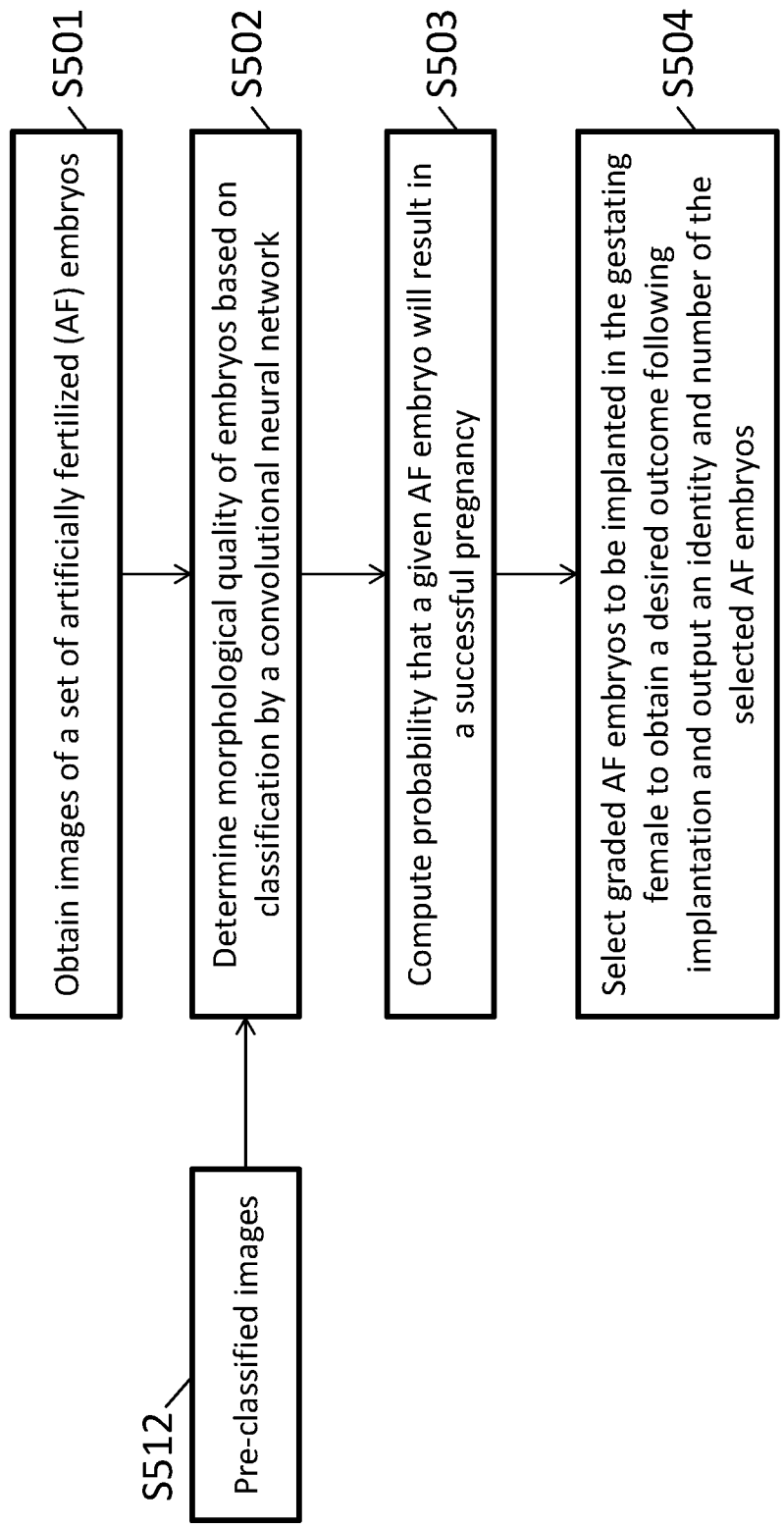
FIG. 5 illustrates a flow chart for a method of classifying human blastocysts in accordance with an implementation.

FIG. 5 illustrates a flow chart for a method of classifying human blastocysts in accordance with an implementation. The method includes, at S501, obtaining images of a set of artificially fertilized (AF) embryos. In an implementation, the images are obtained from an incubator designed to incubate human embryos. The incubator may be equipped with a built-in microscope (e.g., microscope 115) and a camera (e.g., camera 117) to image the embryos while being incubated. The images may include time-lapse images captured at certain pre-determined time periods such as, for example, every 10 minutes, every 15 minutes, every 20 minutes, every hour, etc. In some implementations, the images include images of several planes, e.g., 7 different planes, of the embryos obtained by changing the depth of focus of the microscope. In an implementation, the images are obtained from an incubator such as the incubator 110 described with reference to FIG. 1 above.

At S502, a morphological quality of the embryos is determined based on a classification of the images obtained at S501 using a convolutional neural network (CNN), and each of the embryos is given a grade such as, for example, good, fair or poor. In an implementation, the convolutional neural network is based on Inception-V1 architecture by Google, Inc. In some implementations, the CNN is trained using raw images (i.e., not pre-processed to segment the embryo) of embryos that are pre-classified, at S512, using, for example, a composite grading system based on one or more clinically accepted grading systems such as, for example, the Veeck and Zaninovic grading system, the Gardner grading system or the Asebir grading system. The CNN may be further trained to classify embryos having certain composite grades into good and poor classes (or e.g., any number of classes depending on the particular scheme of classification being used). The identification of good and poor (or other) classes during the pre-classification training of the CNN may be performed by expert clinicians or by using a separate neural network that analyzes images of embryos for parameters such as for example, blastocyst expansion, cell abundance, conformity in inner cell mass (ICM), trophectoderm (TE) and/or zona pellucida (ZP).

It must be noted that while the method described herein uses CNN, any other deep neural network or other types of artificial intelligence or machine learning techniques may be used to determine the morphological quality of the embryos.

In some implementations, at S502, for example, a given embryo is graded as good if the morphological quality indicates that the embryo, upon implantation, will have a morphological quality-based probability of successful pregnancy greater than an upper threshold value, e.g., 60%. On the other hand the embryo is graded as poor if the morphological quality indicates that the embryo, upon implantation, will have a morphological quality-based probability of successful pregnancy lesser than a lower threshold value, e.g., 30%. Thus, in some implementations, an additional grade (e.g., fair) of embryos may be included to indicate a morphological quality-based probability of successful pregnancy between the upper and lower threshold values. In an implementation, the morphological quality of the embryos and the associated grade is determined using, for example, the morphological quality evaluation module 122 described with reference to FIG. 1.

Referring back to FIG. 5, the method further includes, at S503, for each of the embryos graded at S502, a probability that a given graded embryo will result in a successful pregnancy after the given embryo is implanted in a gestating female is computed based on the grade of the given embryo and clinical parameters associated with the gestating female. The clinical parameters include, without limitation, age of the gestating mother, incidence of clinical conditions such as diabetes, obesity, etc. in the gestating female, genetic history of the gestating female, etc.

The probability of successful pregnancy as referred to herein describes the probability that following implantation of a given embryo into the gestating female, resulting pregnancy ends in a live birth. Morphological quality alone may not be a good determinant of the probability of successful pregnancy. Thus, clinical parameters associated with the gestating female are also included when computing the probability of successful pregnancy. In an implementation, the probability of successful pregnancy is computed using a hierarchical type class decision tree such as, for example a CHAID algorithm described with reference to FIG. 3. In such implementations, probability "boxes" are defined using available clinical data for previously graded embryos and computing the probability based on one or more clinical parameters such as, for example, age, associated with the gestating female. For example, an embryo graded as poor may have been found to provide a 35% probability of successful pregnancy when implanted in a 39 year old gestating female, while another embryo graded as poor may have been found to provide a 55% probability of successful pregnancy when implanted in a 32 year old gestating female. Thus, a given embryo may be classified as belonging to a particular probability "box" (e.g., one of the 13.8%, 30.0%, 42.2%, 25.5%, 58.5%, 49.8%, or 66.3% probability categories illustrated in FIG. 3) based on its grade (e.g., good or poor in the example of FIG. 3) and the age (or one or more other clinical parameters) of the gestating female.

At S504, one or more graded embryos to potentially be implanted in the gestating female are selected from the set of embryos of which images were obtained at S501. The one or more graded embryos are selected based on the probability of successful pregnancy (e.g., the probability corresponding to the probability "box" into which the given embryo was classified) for each of the graded embryo computed at S503 and a desired outcome following implantation in the gestating female. For example, a 29 year old gestating female may want twins following implantation. In such a case, from a set of 7 embryos, two or more embryos with high composite probabilities of successful pregnancy may be selected for implantation. The identity of the selected embryos and the number of the selected embryos is then output to, for example, a display device such as a computer monitor, for the benefit of the clinician, who may then exercise his/her judgement in consultation with the gestating female to act on the recommendation about the number and identity of embryos to implant.

In an aspect of the present disclosure, the method described with reference to FIG. 5 may be implemented using a data processing system 120 described with reference to FIG. 1. Accordingly, various computer readable instructions to implement various aspects of the method described with reference to FIG. 5 can be provided on a non-transitory computer readable medium. For example, in one implementation, computer readable instructions to implement S501 using the input module 121, S502 using the morphological quality evaluation module 122, S503 using a pregnancy success computing module 123, and S504 using an embryo selection module 124 may be stored on a non-transitory computer readable medium.

A non-transitory computer readable medium may include, without limitation, a device with fixed storage or a device for reading removable storage media. Examples include all forms of non-volatile memory, media and memory devices, semiconductor memory devices, magnetic disks, magneto optical disks, optical disks, etc.

Experimental Results

To support the techniques described above, experiments were conducted to classify embryos using the morphological quality determined by artificial intelligence.

The study included 10,148 embryos from Center for Reproductive Medicine at Weill Cornell Medicine (2012/May-2017/December). This dataset is referred to herein as WCM-NY. The details of the system used to capture images of the embryos included in the set are as follows: EmbryoScope® time-lapse system (Vitrolife, Sweden); built-in microscope: Leica 20×, 0.40 LWD Hoffman modulation contrast objective specialized for 635 nm illumination; camera resolution: 1280_1024 pixels, three pixels per μm, monochrome, 8-bit; embryo illumination: 0.032s per image using single red LED (635 nm) gives 34 μW cm$^2$ for image acquisition; time between acquisitions: 15-min. cycle time for seven focal planes representing a total of 50,392 images (stored in jpg, 500500 pixels) with about seven focal depths (+45, +30, +15, 0, −, −30, and −45) captured precisely 110 hours post-insemination (hpi) (FIG. 2). The standardization of images by the EmbryoScope software was consistent, and the images were labeled using the Veeck and Zaninovic grading system. In addition, these images contain 130 various grades, of which most comprise a few image numbers (Table 2). Images that were either very dark or missing a picture of an embryo were eliminated from the dataset, and a balanced set of images for both good and poor classes were selected. The Veeck and Zaninovic grading system (Table 2) is a slightly modified version of the Gardner system, classifying embryos based on blastocyst expansion (grades 1 to 6), cell abundance, and conformity in the ICM (grades A, B, and C) and TE (grades A, B, and C) (Table 3).

In addition to the WCM-NY data, two other datasets from the Universidad de Valencia and the Institute of Reproduction and Developmental Biology of Imperial College (IRDB-IC) were used. The data from the Universidad de Valencia was graded based on a slightly different scoring system known as Asebir. Compared to the Gardner system. Asebir uses five rather than six expansion categories and changes the ICM and TE rating terminology to single A, B, C, and D letters (Table 2). The IRDB-IC data was graded using the Gardner scoring system.

The WCM-NY embryos and clinical information from a subset of these embryos, such as grades and patient age were used. The images were divided into training, validation, and test groups. About 70% of the images were allocated to the training group and the remaining 30% to the validation and test groups. The training, validation, and test sets did not overlap.

In this implementation, a DNN for embryo image analysis based on Google's Inception-V1 architecture, which offers a very effective run-time and computational cost was used. To train this architecture, transfer learning was used. A pre-trained network was used and all outer layers were fine-tuned using the WCM-NY images. This transfer learning approach was compared to training the network from scratch.

TABLE 2

Characteristics of 130 various grades and their image numbers.

| The morphological grades | Class size |
| --- | --- |
| 1-2B-/CB, 1-2B-/CB-/C, 1-2B-C, 1-2BA-, 1B-/CB-/C, 1BC, 1CB-/C, 1CC, 2-2B-C, 2-3B-A-, 2-3BA, 2-3BC, 2AA, 2AB-/C, 3-4AA, 3A-B-/C, 3B-/CA, 3B-B-/B, 3BC, 3CA-, 3CB, 3CB-, 3CC, 4A-A, 4A-A-, 4AB-, 4B-/CB, 4B-/CB-, 5A-B, 5AA-, 5BA, 5BA-, 5BB-, 1-2A-B-, 1-2B-/CB-, 1B-/CB, 1B-/CB-, 1B-/CC, 2-3AA, 2-3AA-, 2-3B-/CB, 2-3B-/CB-, 2A-B-/C, 2B-/CB, 2BA, 3A-C, 3B-/CB-/C, 3B-/CC, 4B-B-, 4BB-, 5B-B, 1-2BB-/C, 1AB, 2B-/CB-/C, 3B-C, 4AB, 4B-B, 5A-A-, 5BB, 6BB, 1BB-/C, 1BB-/C, 1-2B-B-/C, 1A-B-, 1B-C, 2-3AB-, 2-3BB-/C, 4A-B, 4AA-, 4BA-, 2-3B-B-/C, 2A-A-, 2B-/CB-, 3B-A, 4AA, 2-3BA-, 1-2A-B, 1A-B, 2BA-, 3B-/CB-, 2AB, 5B-B-, 2AB-, MOR | Less than 10 images per grade |
| 2-3A-B-, 3B-/CB, 2A-B-, 2BB-/C, 3B-A-, 4BB, 2-3AB, 2-3A-A-, CM, CAVM, 1B-B-/C, 2B-B-/C, 3BB-/C, 3BA, 3B-B-/C, 2A-B, 1-2B-B | More than 10 and less than 50 images per grade |
| 2-3A-B, 1-2B-B-, 2-3B-B-, 3A-A, 1-2BB-, 3AB-, 2-3B-B | More than 50 and less than 100 images per grade |
| 1B-B, 1BB-, 2-3BB-, 1-2BB, 1B-B-, 3A-B-, 3AA, 2B-B, 3BA-, 3AA-, 2B-B-, 2-3BB, 3AB, 2BB-, 3B-B-, 1BB, 3A-A- | More than 100 and less than 500 images per grade |
| 2BB, 3B-B, 3BB-, 3A-B, 3BB | More than 500 images per grade |

TABLE 3

Information about how composite grades are provided in different grading systems.

| Objects | Veeck and Zaninovic | Gardner | Asebir |
| --- | --- | --- | --- |
| Expansion | CM | 1 | BT |
| | 1 | 2 | BT |
| | 2 | 3 | BC |
| | 3 | 4 | BE |
| | 4 | 5 | BHi |
| | 5 | 6 | BH |
| ICM | A | A | A |
| | B | A/B | B |
| | C | B/C | C |
| | D | C | D |
| TE | A | A | A |
| | B | A/B | B |
| | C | B/C | C |
| | D | C | D |

In one implementation of the method of classifying human blastocysts described herein, also referred to herein as the STORK framework, Tensorflow version 1.4.0 and the Python library TF-Slim for defining, training, and evaluating models in TensorFlow were used. All training of the deep learning methods was performed on a server running the SMP Linux operating system.

To evaluate the performance of the methods described herein, an accuracy measure, which is the fraction of correctly identified images was used. The accuracy was formally defined as $TNu/(TNu+FNu)$, where TNu (true number) and FNu (false number) are the number of correctly and incorrectly classified images.

To assess the performance of different algorithms, precision-recall curves (PRCs) were used. Here, precisions and recalls are presented by average for multi-class datasets. Additionally, receiver operating characteristics (ROCs) were estimated. The ROC curve is depicted by plotting the true positive rate (TPR) versus the false positive rate (FPR) at various threshold settings. The accuracy is measured by the area under the ROC curve (AUC).

In one implementation, pre-classified images were classified by trained embryologists, who evaluated embryo quality using an internal scoring system with 130 distinct classes. To enable the AI analysis, the 10,148 embryos were subsequently classified into three major groups (good-quality=1,345 embryos, fair-quality=4,062 embryos, and poor-quality=4,741 embryos). An Inception-V1 deep learning-based algorithm was trained using the two quality groups at both ends of the spectrum (i.e., good and poor). The Inception-V1 architecture is a transfer learning algorithm, and fine-tuning of the parameters for all of the layers was performed separately. Upon preprocessing and removal of bad-quality images and random selection of balanced sets of images, 12,001 images with up to seven focal depths (+45, +30, +15, 0, −15, −30, and −45) of good-quality (6,000 images, 877 embryos) and poor-quality (6,001 images, 887 embryos) labels were left. 50,000 steps were used for training the DNN. The performance of STORK was then evaluated using a randomly selected independent test set with 964 good-quality (141 embryos) and 966 poor-quality embryo (142 embryos) images.

Results of the experiment showed that the trained algorithm was able to identify good-quality and poor-quality images with 96.94% accuracy (1,871 correct predictions out of 1,930 images=96.94% accuracy) when tested on 964 good-quality and 966 poor-quality embryo images.

To measure the accuracy of STORK for embryos with multiple image focal depths, a simple voting system was used. If the majority of images from the same embryo were good, then the final quality of the embryo was considered good. For a small number of cases in which the number of good and poor images was equal (e.g., three good and three poor when the number of focal depth was 6), STORK's output probability scores were used to break the tie. The average STORK probability scores of the good images were compared with the average probability scores of the poor images.

97.53% accuracy (276 correct predictions out of 283 embryos=97.53% accuracy; comprises 283 embryos) was observed as a blind test set. It was found that training an Inception-V1 model without fine-tuning did not affect performance. This observation was in agreement with previous studies using similar deep learning techniques.

It was further found that by using STORK to classify the fair-quality embryo images (4,480 images from 640 embryos) as either good or poor, 82% (526 embryos) and 18% (114 embryos) of the embryos were predicted to be good-quality and poor-quality, respectively. Attesting to the intermediate status of the fair group, the average probability score was 0.98 for good-quality and 0.93 for poor-quality classes, which is significantly (p-value <0.01) lower than the probability scores for good and poor images (0.99 on average). Because Inception-V1 was trained for good and poor classes with different implantation probabilities (an approximately 58% and 35% chance of pregnancy for good and poor classes, respectively), it was investigated whether STORK nonetheless produced relevant predictions within the fair class. A closer look showed that embryos with fair-quality images that were classified as poor by STORK had a lower likelihood of positive live-birth (50.9%) as compared to those classified as good (61.4% positive live-birth, while the statistical significance of this difference in outcome has a p-value of <0.05 by the two-tailed Fisher's test).

In addition, it was found that fair embryos predicted to be good quality by STORK came from younger patients (33.98 years old on average) than those predicted to be poor quality (34.25 years old on average). Interestingly, these numbers were similar to the good-quality and poor-quality ages, which are significantly different (p-value <0.01): 33.86 and 34.72 years old on average, respectively. This suggests that STORK finds sufficient structure within embryos classified as fair to make clinically relevant predictions.

It is known that factors such as embryo quality, maternal age, the patient's genetic background, clinical diagnosis, and treatment-related characteristics can affect the pregnancy outcome.

Because embryo quality is one of the most important of these factors, the ultimate aim of any embryo-assessment approach is to identify embryos that have the highest implantation potential, resulting in live-birth. The possibility of predicting the likelihood of pregnancy based on the morphological quality of embryos by using images labeled as "positive" or "negative live-birth" was explored.

It was investigated as to what extent pregnancy rate is associated with embryo morphological quality. To address this question, WCM-NY images associated with 1,620 embryos which the pregnancy outcome (live-birth) information was available were used. 85% of the embryos (1,377 embryos, 9,639 images) were allocated to build two classes—"negative live-birth" (603 embryos) and "positive live-birth" (774 embryos)-as training. There were good- and poor-quality embryos in both the "negative live-birth" and "positive live-birth" classes. Thus, embryo images with four different characteristics in two classes were available.

A new training algorithm, different from STORK, called DCNN (deep convolutional neural network) to fine-tune the Inception-V1 algorithm using two classes (positive and negative live-birth) with 50,000 steps was built. The DCNN was tested with 243 randomly selected embryos as a blind test comprising 136 and 107 "positive" and "negative" embryos (1,701 images), respectively. 51.85% accuracy was obtained for discretization of positive and negative live-birth. This suggests that discretization of images based on live-birth outcome using embryo morphology alone cannot be useful since other important characteristics, such as the patient's age and genetic or clinical variations, can affect the pregnancy rate. Therefore, an alternative method for predicting pregnancy probability based on a decision tree method that integrates clinical information and embryo quality was investigated.

For this purpose, a hierarchical type class decision tree—the chi-squared automatic interaction detection (CHAID) algorithm was used. A CHAID decision tree was designed using all 2,182 embryos from the WCM-NY database with available clinical information that treated through IVF treatment types. The interaction between patient age (consisting of seven classes: ≤30, 31-32, 33-34, 35-36, 37-38, 39-40, and >41) and embryo quality (consisting of two classes: good and poor), and their effect on live-birth outcome was then investigated. The CHAID algorithm can project interactions between variables and non-linear effects, which are generally missed by traditional statistical techniques. CHAID builds a tree to determine how variables can explain an outcome in a statistically meaningful way. CHAID uses $X^2$ statistics through the identification of optimal multi-way splits, and identifies a set of characteristics (e.g., patient age and embryo quality) that best differentiates individuals based on a categorical outcome (here, live-birth) and creates exhaustive and mutually exclusive subgroups of individuals. It chooses the best partition on the basis of statistical significance and uses Bonferroni-adjusted p-values to determine significance with a predetermined minimum size of end nodes. A 1% Bonferroni-adjusted p-value, a maximum depth of the tree (n=5), and a minimum size of end nodes (n=20) were used as the stopping criteria.

It must be noted that while several other classification algorithms could have been employed for the prediction, CHAID was the best fit in terms of model quality criteria, and it enabled a more proper visualization of the decision tree diagram. As FIG. 3 shows, patients were classified into three age groups: (i) ≤36, (ii) 37 and 38, and (iii) ≥39 years old. For each age group, embryos were discretized in good- and poor-quality groups.

The results confirm the association between pregnancy probability and patient age. The pregnancy probability for patients with good-quality embryos is significantly (1% Bonferroni-adjusted p-value) higher than that for patients with poor-quality embryos across different ages. FIG. 3 indicates that patients ≤36 years old have a higher pregnancy rate compared to patients in the other two age groups.

Implementations of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs embodied on a tangible medium, i.e., one or more modules of computer program instructions, encoded on one or more computer storage media for execution by, or to control the operation of, a data processing apparatus. A computer storage medium can be, or be included in, a computer-readable storage device, a computer-readable storage substrate, a random or serial access memory array or device, or a combination of one or more of them. The computer storage medium can also be, or be included in, one or more separate components or media (e.g., multiple CDs, disks, or other storage devices). The computer storage medium may be tangible and non-transitory.

The operations described in this specification can be implemented as operations performed by a data processing apparatus on data stored on one or more computer-readable storage devices or received from other sources. The operations may be executed within the native environment of the data processing apparatus or within one or more virtual machines or containers hosted by the data processing apparatus.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other system suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers or one or more virtual machines or containers that are located at one site or distributed across multiple sites and interconnected by a communication network. Examples of communication networks include a local area network ("LAN") and a wide area network ("WAN"), an inter-network (e.g., the Internet), and peer-to-peer networks (e.g., ad hoc peer-to-peer networks).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

The invention claimed is:

1. A method for classifying human blastocysts, comprising:
   obtaining images of a set of artificially fertilized (AF) embryos incubating in an incubator;
   determining a morphological quality of the AF embryos based on a classification of the images by a convolutional neural network trained using images of pre-classified embryos and grading each of the AF embryos based on the morphological quality, wherein the convolutional neural network is trained using the pre-classified embryos and clinical data associated with the pre-classified embryos, the clinical data associated with the pre-classified embryos comprising an age of a donor female providing eggs that were fertilized to obtain the pre-classified embryos and a presence of clinical conditions associated with the donor female, the clinical conditions including diabetes and obesity;
   computing a probability that a given graded AF embryo will result in a successful pregnancy after the given AF embryo is implanted in a gestating female for each of the AF embryos from the set based on a grade of the given AF embryo and clinical parameters associated with the gestating female;
   selecting graded AF embryos to be recommended to be implanted in the gestating female from the set based on the probability of successful pregnancy and an outcome desired by the gestating female following implantation and outputting an identity and number of the selected AF embryos.

2. The method of claim 1, wherein the images are obtained at one or more predetermined points in time after fertilization.

3. The method of claim 1, wherein the images include images of multiple planes of the AF embryos.

4. The method of claim 1, wherein the selected AF embryos provide the highest likelihood of live birth following implantation of the selected AF embryos in the gestating female.

5. The method of claim 1, wherein the morphological quality of the AF embryos is classified as good, fair and poor.

6. The method of claim 1, wherein the images of pre-classified embryos used for training the convolutional neural network include images of pre-classified embryos taken at two different times post-fertilization and at seven different planes across each of the pre-classified embryos.

7. The method of claim 6, wherein the images of pre-classified embryos are classified as good, fair and poor.

8. The method of claim 1, wherein the images of the set of AF embryos are unprocessed bright field images using a Hoffman modulation contrast objective.

9. The method of claim 1, wherein the clinical parameters associated with the gestating female include an age of the gestating female and a presence of clinical conditions associated with the gestating female, obesity.

10. A system for classifying human blastocysts, comprising;
an input module configured to receive images of a set of artificially fertilized (AF) embryos incubating in an incubator;
a morphological quality evaluation module configured to determine a morphological quality of the AF embryos based on a classification of the images by a deep neural network trained using images of pre-classified embryos, wherein the deep neural network is trained using the pre-classified embryos and clinical data associated with the pre-classified embryos, the clinical data associated with the pre-classified embryos comprising an age of a donor female providing eggs that were fertilized to obtain the pre-classified embryos and a presence of clinical conditions associated with the donor female, the clinical conditions including diabetes and obesity;
a pregnancy success computing module configured to compute a probability that a given AF embryo will result in a successful pregnancy after the given AF embryo is implanted in a gestating female for each of the AF embryos from the set based on the morphological quality of the AF embryos and clinical parameters associated with the gestating female; and
an embryo selection module configured to select one or more of the AF embryos from the set based on the probability of successful pregnancy, and to output an identity of each of the selected AF embryos and a number of the selected AF embryos to be recommended to be implanted in the gestating female based on a desired outcome input into the embryo selection module following implantation.

11. The system of claim 10, wherein the deep neural network is a convolutional neural network and the images of the pre-classified embryos are unprocessed bright field micrographs of the pre-classified embryos.

12. The system of claim 10, wherein the images of the AF embryos and the images of the pre-classified embryos are monochrome images.

13. The system of claim 10, wherein the embryo selection module is configured select AF embryos that provide a highest likelihood of live birth following implantation of the AF embryos in the gestating female.

14. The system of claim 10, wherein the number of the selected AF embryos to be implanted into the gestating female is determined by the embryo selection module based on ab a combination of the number and the identity of selected AF embryos which will result in a highest likelihood of live birth following implantation of the AF embryos in the gestating female.

15. The system of claim 10, wherein the clinical parameters associated with the gestating female include an age of the female and a presence of clinical conditions including diabetes and obesity.

16. A non-transitory computer readable medium storing a computer readable program of classifying human blastocysts, comprising;
computer readable instructions to determine a morphological quality of artificially fertilized (AF) embryos based on a classification of images of the AF embryos by a convolutional neural network trained using images of pre-classified embryos, wherein the convolutional neural network is trained using the pre-classified embryos and clinical data associated with the pre-classified embryos, the clinical data associated with the pre-classified embryos comprising an age of a donor female providing eggs that were fertilized to obtain the pre-classified embryos and a presence of clinical conditions associated with the donor female, the clinical conditions including diabetes and obesity;
computer readable instructions to compute a probability that a given AF embryo will result in a successful pregnancy after the given AF embryo is implanted in a gestating female for each of the AF embryos, the probability being computed based on the morphological quality of the given AF embryo and clinical parameters associated with the gestating female; and
computer readable instructions to select one or more of the AF embryos based on the morphological quality of the AF embryos and clinical parameters associated with the gestating female, and provide an identity and number of AF embryos that will provide the highest likelihood of live birth following implantation in the gestating female.

17. The non-transitory computer readable medium of claim 16, wherein the clinical parameters associated with the gestating female include an age and a presence of clinical conditions including diabetes and obesity.

18. The non-transitory computer readable medium of claim 16, wherein the number of the selected AF embryos to be implanted into the gestating female is determined by the embryo selection module based on a combination of the number and identity of selected AF embryos which will result in a highest likelihood of live birth following implantation of the AF embryos in the gestating female.

19. The non-transitory computer readable medium of claim 16, wherein the convolutional neural network is trained using the images of the pre-classified embryos and clinical data associated with the pre-classified embryos.

* * * * *